US007495019B2

United States Patent
Zeng

(10) Patent No.: US 7,495,019 B2
(45) Date of Patent: Feb. 24, 2009

(54) BENZOISOSELENAZOLE DERIVATIVES WITH ANTI-INFLAMMATION, ANTIVIRUS AND ANTITHROMBOSIS ACTIVITY AND THEIR USE

(75) Inventor: Huihui Zeng, Beijing (CN)

(73) Assignee: Peking University, Beijing (CN)

(*) Notice: Subject to any disclaimer, the term of this patent is extended or adjusted under 35 U.S.C. 154(b) by 296 days.

(21) Appl. No.: 10/479,883

(22) PCT Filed: Jun. 10, 2002

(86) PCT No.: PCT/CN02/00412

§ 371 (c)(1), (2), (4) Date: Aug. 27, 2004

(87) PCT Pub. No.: WO03/095436

PCT Pub. Date: Nov. 20, 2003

(65) Prior Publication Data

US 2005/0014801 A1 Jan. 20, 2005

(30) Foreign Application Priority Data

Jun. 8, 2001 (CN) ................................ 01 1 18666

(51) Int. Cl.
*A61K 31/41* (2006.01)
*C07D 421/10* (2006.01)
*C07D 517/04* (2006.01)

(52) U.S. Cl. ...................................... 514/359; 548/121

(58) Field of Classification Search ................. 514/359; 548/121

See application file for complete search history.

(56) References Cited

U.S. PATENT DOCUMENTS

| | | | | | |
|---|---|---|---|---|---|
| 4,418,069 | A | * | 11/1983 | Welter et al. | 514/359 |
| 4,550,168 | A | * | 10/1985 | Welter et al. | 546/268.4 |
| 4,711,961 | A | * | 12/1987 | Welter et al. | 548/121 |
| 4,774,252 | A | * | 9/1988 | Welter et al. | 514/359 |
| 4,778,814 | A | * | 10/1988 | Cash | 514/359 |
| 5,008,394 | A | * | 4/1991 | Gunther et al. | 548/121 |
| 5,683,863 | A | * | 11/1997 | Bergthaller et al. | 430/613 |

OTHER PUBLICATIONS

STN HCAPLUS Document No. 130:66559. Mlochiowski et al., "Some developments in the Chemistry of Selenium Heterocycles and Related Diselenides" Blue Danube Symposium on Heterocyclic Chemistry: Abstracts and Short Papers, 7th, Eger, Hung, Jun. 7-10, 1998 (1998) Paper 120/1-Paper 120/5.*

STN Document No. 135:195627, Osajda, et al. Polish Journal of Chemistry (2001), 75(6), pp. 823-830.*

Lesser, Beilstein Citation 2-27-00-00222—Chemische Berichte, 57, (1924), p. 1079.*

Osajda et al., Polish Journal of Chemistry, (Jun. 29, 2001), 75(6), pp. 823-830.*

Golub et al., Science, vol. 286, Oct. 15, 1999, pp. 531-537.*

* cited by examiner

*Primary Examiner*—Laura L. Stockton
(74) *Attorney, Agent, or Firm*—Pillsbury Winthrop Shaw Pittman LLP

(57) ABSTRACT

The present invention relates to new bisbenzisoselenazolonyl derivatives of the following general formulae (I), (II) or (III) and their pharmaceutically acceptable salts. The inventive derivatives have antineoplastic, anti-inflammatory and anti-thrombotic activities (I)

O O N—R—N Se Se (II)

O N—R′ Se (III)

$NH_2$ O O Pt N R'''' . $NH_2$ O=C Se

7 Claims, No Drawings

BENZOISOSELENAZOLE DERIVATIVES WITH ANTI-INFLAMMATION, ANTIVIRUS AND ANTITHROMBOSIS ACTIVITY AND THEIR USE

FIELD OF THE INVENTION

The present invention relates to new benzisoselenazolonyl derivatives having antineoplastic, anti-inflammatory and antithrombotic activities as well as their use. Also, the present invention relates to a pharmaceutical composition comprising the benzisoselenazolonyl derivatives, their use in manufacturing a medicament and a method for treating inflammation and cancer diseases and preventing thrombosis.

BACKGROUND OF THE INVENTION

Many researches focus on the remedy containing selenium because the selenium element has important functions in biologic body. But problem is inorganic selenium is difficult to absorb, and keeps a short time in blood, low activity and high toxicity. Compared with the characteristics of inorganic selenium, those of organoselenium compound have been improved very much.

Selenium is an important trace element. Deficiencies of selenium (<0.1 ppm) for a long time may induce various diseases, including hepatonecrosis, cardiac muscle injury, cancer, and rheumatic diseases.

So far, it has been known that Benzisoselenazolones (BISA), functioning in a GSH-Px-like way, inhibit in vitro the lipid peroxidation of microsome and have an effect in preventing the body from the peroxidation injuries. 2-phenyl-(1, 2)-benzisoselenazol-3(2H)-on (Ebselen) of the following formula is the best one of GSH-Px-like compounds with high anti-oxidative activity and low toxicity (LD50>6810 mg/Kg, mice):

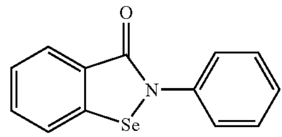

Many researches are concentrated on modifying ebselen to improve its antineoplastic activity, but no successful antineoplastic active compound based thereon is reported up to now. Therefore, the object of the present invention is to modify ebselen to form new bisbenzisoselenazolonyl derivatives having higher anti-inflammatory activity, broader compatibility and lower toxicity. Meanwhile, antineoplastic organoselenium compounds having "biological response regulator" characteristic are obtained through modifying ebselen.

SUMMARY OF THE INVENTION

According to one aspect of the invention, there is provided bisbenzisoselenazolonyl derivatives of general formulae (I)), (II) or (III) and their pharmaceutically acceptable salts:

(I)

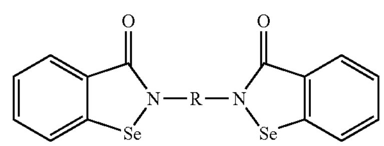

(II)

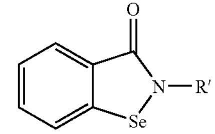

(III)

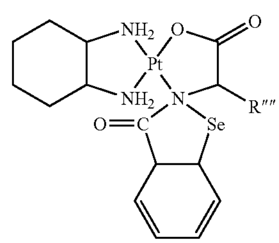

wherein:

R is $C_{1-6}$-alkylene, phenylidene, biphenylidene, triphenylidene, or the following group:

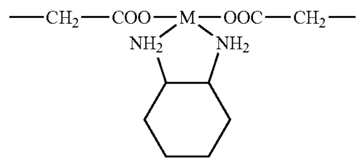

wherein: M=Pt, Pd or Rh;

R' is a saccharide residue or the following group:

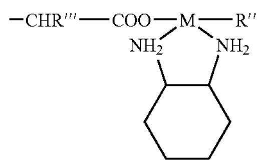

wherein: R" is Cl, $H_2O$, OH, Br, or I,

R''' is —H, —$CH_2C_6H_5OH$, —$CH_2OH$, —$CH_2CONH_2$, —$CH_2CH_2COOH$ —$CH_2(CH_2)_4NH_2$, —$CH_2COOH$, —$CH_2CH_2CONH_2$, —$(CH_2)_3CH$, —$(CH_2)_3NHC(NH)NH_2$, —$(CH_2)_3CHCH_2$, —$CH_3$, —$CH_2CH_3$, —$CH_2C_6H_5$, —$CH_2SH$, Or —$CH_2CH_2SCH_3$,

R'''' is —H, —$CH_2C_6H_5OH$, —$CH_2OH$, —$CH_2CONH_2$, —$CH_2CH_2COOH$ —$CH_2(CH_2)_4NH_2$, —$CH_2COOH$, —$CH_2CH_2CONH_2$, —$(CH_2)_3CH$, —$CH_2)_3NHC(NH)NH_2$, —$CH_2)_3CHCH_2$, —$CH_3$, —$CH_2CH_3$, —$CH_2C_6H_5$, —$CH_2SH$, or —$CH_2CH_2SCH_3$.

According to another aspect of the present invention, there is provided a pharmaceutical composition comprising as an active ingredient the above compounds (I), (II) or (III) or their pharmaceutically acceptable salts and any pharmaceutically acceptable excipient or carrier.

According to still another aspect of the present invention, there is provided the use of the bisbenzisoselenazolonyl derivatives of general formulae (I), (II) or (III) or their pharmaceutically acceptable salt in manufacturing a medicine for the treatment of cancer and inflammatory diseases or preventing thrombosis.

According to still another aspect of the present invention, there is provided a method for treating inflammatory and cancer diseases or preventing thrombosis in mammal including human being, comprising the step of administering therapeutically effective dosage of the bisbenzisoselenazolonyl derivatives of general formulae (I), (II) or (III) or their pharmaceutically acceptable salt to the patients in need of treatment.

According to still another aspect of the present invention, there is provided a method for treating inflammatory and cancer diseases or preventing thrombosis in mammal including human being, comprising the step of administering therapeutically effective dosage of the bisbenzisoselenazolonyl derivatives of general formulae (I), (II) or (III) or their pharmaceutically acceptable salt in combination with other anti-inflammatory or antineoplastic agents to the patients in need of treatment.

DETAILED DESCRIPTION OF THE INVENTION

The benzisoselenazolonyl derivatives according to the invention are designed under the consideration of active pharmacore of ebselen and enhancing the function group. Due to the characteristics of the structure, the inventive compounds have multitargets in biologic body and therefore exhibit multiple biological activities. The fact that the compounds are antineoplastic agents functioned as a biological response modifier besides the inhibition action to cancer makes them a novel antineoplastic agent.

According to one embodiment of the invention, there is provided bisbenzisoselenazolonyl derivatives of general formulae (I)), (II) or (III) and their pharmaceutically acceptable salts:

(I)

(II)

(III)

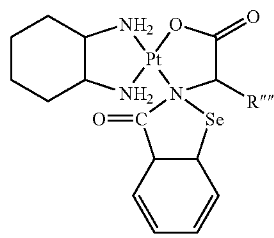

wherein:

R is $C_{1-6}$-alkylene, phenylidene, biphenyliden, triphenylidene, or the following group:

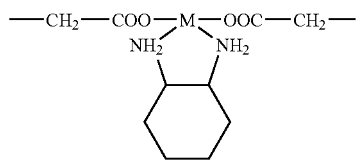

wherein: M=Pt, Pd or Rh;

R' is a saccharide residue Or the following group:

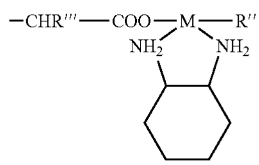

wherein: R" is Cl, $H_2O$, OH, Br, or I,

R'" is —H, $—CH_2C_6H_5OH$, $—CH_2OH$, $—CH_2CONH_2$, $—CH_2CH_2COOH$ $—CH_2(CH_2)_4NH_2$, $—CH_2COOH$, $—CH_2CH_2CONH_2$, $—(CH_2)_3CH$, $—(CH_2)_3NHC(NH)NH_2$, $—(CH_2)_3CHCH_2$, $—CH_3$, $—CH_2CH_3$, $—CH_2C_6H_5$, $—CH_2SH$, Or $—CH_2CH_2SCH_3$,

R"" is —H, $—CH_2C_6H_5OH$, $—CH_2OH$, $—CH_2CONH_2$, $—CH_2CH_2COOH$ $—CH_2(CH_2)_4NH_2$, $—CH_2COOH$, $—CH_2CH_2CONH_2$, $—(CH_2)_3CH$, $—(CH_2)_3NHC(NH)NH_2$, $—(CH_2)_3CHCH_2$, $—CH_3$, $—CH_2CH_3$, $—CH_2C_6H_5$, $—CH_2SH$, or $—CH_2CH_2SCH_3$.

In this embodiment, preferred compounds are bisbenzisoselenazolonyl derivatives of the general formula (I), wherein R is a $C_{1-4}$-alkylene, phenylidene or biphenylidene group. Particularly preferred are compounds wherein R is $C_2$-alkylene or biphenylidene group.

Preferred for R' is a 1,3,4,6-tetra-O-acetyl-2-deoxy-D-glucopyranosyl group.

Preferred for R'" and R"" independently represent —H, $—CH_3$, $—CH_2CH_3$, $—CH_2C_6H_5$, $—CH_2SH$, or $—CH_2CH_2SCH_3$.

The benzisoselenazolonyl derivatives according to the present invention can be synthesized according, to any process known to the skilled in the art or the process described in the specification of the application. For example, 2-(chloroseleno)benzoyl chloride is reacted with corresponding diamine or amino saccharide in appropriate organic solvent under cool and nitrogen atmosphere, then separated using standard procedure known to the skilled in the art to obtain the desired compound.

The benzisoselenazolonyl derivatives according to the invention wherein R or R' is a metal complex can be synthesized according to the method known to the skilled in the art by using the platinum compound material.

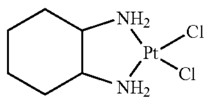

1,2-diaminocyclohexanoplatinum(II)

The benzisoselenazolonyl derivatives according to the present invention or their salts may be administered in form of pure substance or proper pharmaceutical composition comprising the compounds of general formulae (I), (II) or (III) as an active agent optionally in combination with other agents, via any acceptable administration route. Therefore, the invention also includes a pharmaceutical composition comprising the benzisoselenazolonyl derivatives of general formulae (I), (II) or (III) or their pharmaceutically acceptable salts and pharmaceutically acceptable exipient or carrier, which can be used for treating inflammatory and cancer diseases or preventing thrombosis.

The inventive compounds or composition can be administered by a number of routes, including but not limited to orally, intranasally, rectally transdermally, or parenterally, in form of solid, semi-solid, lyophilized powder, or liquid. For example, the composition can be used in the form of tablet, suppository, pill, soft and hard gelatin capsule, granule, solution, suspension or aerosol. Preferred is single unit form for exact dosage. The pharmaceutical composition includes conventional excipient or carrier and one or more inventive compounds. The composition may additionally contain other therapeutic agent and the likes.

Generally, depending on the mode of administration, the pharmaceutically acceptable composition may comprise 1 to 99% by weight of the inventive compound as active agent and 99 to 1% by weight of appropriate pharmaceutical excipient. The preferred composition comprises about 5 to 75% by weight of the inventive compound, and the other is appropriate excipient or carrier.

Preferred administration route is by intravenous injection, using conventional daily dosage protocol, which may be adjusted according to the severity of the illnesses. The compounds or their pharmaceutically acceptable salts according to the invention can be formulated into dosage form for injection, for example, dispersing about 0.5 to 50% by weight of the inventive compounds as an active agent in liquid excipient or carrier, such as water, saline, aqueous glucose solution, ethanol and glycerol to for a solution or suspension.

The pharmaceutical composition, which can be administered in form of a solution or suspension, can be obtained, for example, by dissolving or dispersing the inventive compounds (for example, about 0.5 to 20% by weight) and optionally other adjuvants in carriers, including but not limited to water, saline, aqueous glucose solution, ethanol and glycerol solution.

Further, if necessary, the pharmaceutical composition according to the invention may include the assistant substances, such as wetting agent or emulsifier, pH buffer, antioxidant and the likes. The particular examples are citric acid, sorbitan monolaurate, triethanolamine oleate, butylated hydroxybenzene and the likes.

The preparation of the inventive composition may be obtained according to any process well know or obvious to the skilled in the art (for example, see *Remington's Pharmaceutical Sciences*, edition 18, Mack Publishing Company, Easton, Pa., 1990). Anyway, the inventive composition includes the inventive compound in an amount effective for treating the corresponding disease.

According to another aspect of the present invention, there is provided a method for treating inflammatory and cancer diseases or preventing thrombosis in mammal including human being, comprising the step of administering therapeutically effective dosage of the bisbenzisoselenazolonyl derivatives of general formulae (I), (II) or (III) or their pharmaceutically acceptable salt to the patients in need of treatment.

According to still another aspect of the present invention, there is provided a method for treating inflammatory and cancer diseases or preventing thrombosis in mammal including human being, comprising the step of administering therapeutically effective dosage of the bisbenzisoselenazolonyl derivatives of general formulae (I), (II) or (III) or their pharmaceutically acceptable salt in combination with other anti-inflammatory or antineoplastic agents or anti-thrombotics to the patients in need of treatment.

If the inventive bisbenzisoselenazolonyl derivatives are applied together with other anti-inflammatory or antineoplastic agents or anti-thrombotics, they may be administered in sequence or at the same time. For example, the inventive bisbenzisoselenazolonyl derivatives are administered firstly, and then the other anti-inflammatory or antineoplastic agents or anti-thrombotics. Alternatively, the other anti-inflammatory or antineoplastic agents or anti-thrombotics are administered firstly, and then the inventive bisbenzisoselenazolonyl derivatives.

In a preferred embodiment, the other antineoplastic agent includes Cisplatin, Taxol, Cyclophosphamide, Isophosphamide, Methotrexate, Fluorouracil, Epirubicin, Daunomycin, Adriamycin, Mitomycin, Pingyangmycin, Carboplatin, Lomustine, Carmustine or their combinations.

In a preferred embodiment, the other anti-inflammatory agent includes Aspirin Indomethacin, Cephalsosporins, Macroolides or their combinations.

In a preferred embodiment, the other anti-thrombotics includes Aspirin.

The dosage of the benzisoselenazolonyl derivatives according to the invention for cancer diseases is in the range of 0.05-250 mg/kg of body weight; for inflammation diseases is in the range of 1-100 mg/kg of body weight, and for preventing thrombosis is in the range of 1-100 mg/kg.

When combined with other anti-inflammatory or antineoplastic agents or anti-thrombotics, the dosage of the inventive benzisoselenazolonyl derivatives will be reduced greatly, about one-tenth to half of that when used alone.

The More Detailed Description about the Invention are as follows.

EXAMPLE 1

1,2-Bis[(1,2)-benzisoselenazol-3(2H)-onyl]ethane (E003)

1 g of 2-(chloroseleno)benzoyl chloride in tetrahydrofuran was added dropwise to a stirred solution of ethylenediamine of 0.14 ml and triethylamine of 1.29 ml under nitrogen atmosphere while cooling in an ice bath, with white precipitate appearing. After stirring 3 hours, light yellow suspension was formed. The solvent was evaporated in vacuum, and the light yellow residue was sucked off, washed with water, and then recrystallized from DMSO, to obtain the titled compound. Yield: 0.1 g (11%), m.p>320° C.

EI-MS: (m/z)($m^+$)424; $^1$HNMR(DMSO-$d_6$): 7.37-7.98 (8H, m, ArH), 4.02 (4H,s,—$CH_2CH_2$—).

EXAMPLE 2

4,4'-Bis[(1,2)-benzisoselenazol-3(2H)-onyl]-biphenyl (E002)

0.5 g of 2-(chloroseleno)benzoyl chloride in tetrahydrofuran was added dropwise to a stirred solution of biphenyldiamine of 0.182 g and triethylamine of 0.62 ml under nitrogen atmosphere while cooling in an ice bath. After stirring for 3 hours, white precipitate was formed, sucked off; washed with tetrahydrofuran and ethanol. After recrystallization from DMSO, the titled compound was obtained as a light brown precipitate. Yield: 0.1 g (18.2%), m.p.>320° C.

EI-MS: (m/z)($m^+$) 550; $^1$HNMR (DMSO-$d_6$): 7.48-8.12 (m, 16H, ArH).

EXAMPLE 3

2-(1,3,4,6-tetra-O-acetyl-2-deoxy-D-glucopyranosyl)-(1,2)-benzisoselenazol-3(2H)-one (E001)

730 mg of 1,3,4,6-tetra-O-acetyl-D-glucosamine was dissolved in chloroform under nitrogen atmosphere while cooling in an ice bath. The solution of 0.551 g of 2-(chloroseleno) benzoyl chloride in chloroform was dropped slowly thereto under stirring. After 2 hours, the reaction solution was separated on silica gel column with petroleum: ethyl acetate=3:1 as eluent. The titled compound was obtained as a light yellow solid. Yield: 200 mg (18.0%), m.p 73-75° C.

IR 1745(—CO); UV($CHCl_3$) 320 nm, 260 nm (isoselenazol ring).

FAB-MS(m/z) 566.3 (M+K).

$^1$H NMR: δ H(ppm) 7.24-8.12 (4H,m,ArH), 6.20 (1H,d, anomeric H in sugar), 3.97-5.64 (m,6H,sugar:H), 1.82-2.16 (12H,m,—$COCH_3$).

$^{13}$C NMR: δ (ppm) 166.77, 168.66, 169.29, 169.61. 170.44 (—CO), 124.22, 126.28, 128.81, 132.37, 138.30 (carbon in benzene), 91.43, (carbon in sugar, C—I), 60.15, 61.35, 68.35, 71.91, 72.35, (carbon in sugar, C-2,3,4,5,6), 20.34, 20.48, 20.55, 20.78 (—$COCH_3$).

EXAMPLE 4

Synthesis of 1,2-diaminocyclohexanoplatinum-2-glycine-[(1,2)-benzisoselenazol-3(2H)-one]

1) Synthesis of $K_2PtCl_4$

10% aqueous hydrazine solution was added dropwise to a stirred solution of 0.7 g $K_2PtCl_6$ (1.44 mmol) in 7 ml $H_2O$ at 80° C. while stirring completely. The reaction was continued to the formation of a dark red solution. The left $K_2PtCl_6$ and metal platinum was filtered and discarded. The filtrate was concentrated to obtain $K_2PtCl_4$ as red needle crystal. Yield: 0.5 g (84%).

2) Synthesis of 1,2-diaminocyclohexanoplatinum(II)

The solution of $K_2PtCl_4$ (0.2 g, 0.48 mmol) in 2 ml $H_2O$ was mixed with the solution of KI (0.8 g) in 0.6 g $H_2O$ on the boiling water bath while avoiding light irradiation. The temperature was lifted rapidly to 80° C. and kept for 30 min in dark. 0.05 g 1,2-diaminocyclohexane solid was added to the solution, yellow precipitate was formed. The precipitate was sucked off, washed with little ice water, ethanol and diethylether. Yield: 0.21 g (78%)

3) 1,2-diaminocyclohexanoplatinum-2-glycine-[(1,2)-benzisoselenazol-3(2H)-one]

0.02 g of 2-glycine ethylester-[(1,2)-benzisoselenazol-3 (2H)-one] was dissolved in 0.5 ml chloroform. Then, a solution of 15 ml NaOH (1 mol/L) was added thereto. The solution was incubated for 10 hours at 50-60° C. A solution of 15 ml NaOH (1 mol/L) was added again after collecting the yellow aqueous layer to hydrolyze the ester completely. HCl (1 mol/L) was added to acidify the combined aqueous layer, so that the insoluble product of 2-glycine-[(1,2)-benzisoselenazol-3(2H)-one] was precipitated. The insoluble solid was sucked off and dried. Yield: 0.025 g.

0.015 g 1,2-diaminocyclohexanoplatinum was dissolved in 0.15 ml water to form a yellow paste. A solution of $AgNO_3$ (0.009 g) in 0.5 ml $H_2O$ was added to the paste while stirring for 4 hours and avoiding light irradiation. The formed AgI yellow precipitate was discarded, and the residue was washed with little ice water. At this time, no white turbidity would occur if one drop of filtrate was mixed with one drop of 1M KCl.

To 0.015 g of 2-glycine-[(1,2)-benzisoselenazol-3(2H)-one] was added 0.0036 g KOH and 2 ml water to get a yellow suspension. The yellow suspension was mixed with a stirred solution of 1,2-diaminocyclohexanoplatinum for 90 mins in dark, filtered and dried under reduced pressure to get yellow crystal. Yield: 25 mg (50%).

FAB: m/z(M+1) 566, Far-IR 340 $cm^{-1}$ (Pt—O), IR 420 $cm^{-1}$ (Pt—N).

EXAMPLE 5

The Experiment of Growth Inhibition to Cancer Cell by the Compounds

SRB assay (adherent cell) was applied in the example. Cancer cells (3-5×$10^4$ cells/ml) were inoculated in a 96-well plate (180 μl/well) in air with 5% CO2 and saturation humidity at 37° C. for 24h. A solution of 20 μl with different concentrations of test compound to each well, and was continued culturing for an indicated time in air with 5% $CO_2$ and saturation humidity at 37° C. After the indicated time, the culture solution was discarded, and then 100 μl of 10% trichloroactic acid (TCA) was added and placed in refrigerator at 4° C. to fix the cells for 1 hour. The solution was discarded, and the plate was washed with distilled water. After dried by centrifuge, 50 μl of SRB solution (0.4% with 1% HAc) was added to each well, and placed at ambient temperature for 10 minutes. After excess SRB solution was discarded, the 96-well plate was washed with 1% acetate solution 5 times in order to remove the no binding SRB. After dried by centrifuge, the plate was further dried in air. 100 μl of 10 mmol/L Tris solution (pH 10.5, basic, no buffer solution) was added to each well, to dissolve SRB binding with cell completely. After homogenization, the OD value of each well was measured at 540 nm by 96-well microplate reader (TECAN SUNRISE Magellan USA) Here: Data of OD value=OD value (MTT or SRB+cell)−OD value (MTT or SRB, free cell). The OD±SD is for the parallel groups. The cell survive rate and drug inhibition rate were calculated according to the following equations:

Cell survive rate %=(*OD* of treated group/*OD* value of control)×100%

Drug inhibition rate %=[1-(*OD* value of treated group)/*OD* value of control]×100%

According to the above SRB method, E003 was screened in Bel-7402 (human liver cancer cell), KB (human nasopharyngeal cancer cell) and Hela (human cervical carcinoma cell). The results are listed in Tab.1

TABLE 1

| sample | model | index | value | dosage |
|---|---|---|---|---|
| E003 | Ble-7402 | Inhibition rate % | 2.05 | 1 μM |
| | | | 7.28 | 5 μM |
| | | | 58.72 | 10 μM |

TABLE 1-continued

| sample | model | index | value | dosage |
|---|---|---|---|---|
| | | | 82.46 | 50 μM |
| | | | 89.57 | 100 μM |
| E003 | KB | Inhibition rate % | 2.94 | 1 μM |
| | | | 4.61 | 5 μM |
| | | | 25.71 | 10 μM |
| | | | 92.49 | 50 μM |
| | | | 97.46 | 100 μM |
| E003 | HeLa | Inhibition rate % | 4.89 | 1 μM |
| | | | 12.16 | 5 μM |
| | | | 64.12 | 10 μM |
| | | | 86.18 | 50 μM |
| | | | 88.12 | 100 μM |

In addition, $IC_{50}$ of E003 was determined in 9 kinds of human cancer cell lines at different times by using the same method as above. The inhibition effects of E003 for the growth of cancer cell lines were listed in Table 2.

TABLE 2

The inhibition $IC_{50}$ of E003 for the growth of cancer cell lines

| Cell lines | $IC_{50}$ value (μmol/L) | | |
|---|---|---|---|
| | 24 h | 48 h | 72 h |
| HL-60 | 33.03 | 3.773 | 0.1467 |
| K562 | — | 8.507 | 4.24 |
| A549 | 3.920 | 3.600 | 2.904 |
| Calu-3 | 45.41 | 16.77 | 14.18 |
| BGC-823 | 31.92 | 19.07 | 12.97 |
| Bel-7402 | 35.23 | 12.06 | 7.867 |
| Hela | 16.78 | 10.31 | 9.845 |
| MCF-7 | ** | 39.88 | 27.49 |
| KB | ** | 2.067 | ** |

**no data;
—: no $IC_{50}$ value.

EXAMPLE 6

The Effect or the Compound on the Weight of Tumor

Lewis lung cancer tissue was resuscitated and subcultured by standard procedure. A piece of Lewis lung cancer was transplanted into the subcutaneous space on the back of each C57 mouse for inoculation and growth. The Lewis lung cancer cells were dispersed in saline to form a cell suspension of $10^6$/ml. 0.2-0.3 ml of the suspension were inoculated into each C57 mouse Mice were randomized into three groups, 10 for each group. In the treatment group, the mice were injected i.p. with E003 in amount of 50 mg/kg; in reference group, DDp, 2 mg/kg; and in the negative control group (solvent group), 0.5% CMC-Na. The total volume for every group is the same. E003 was administered by i.p. from the second day of transplantation for 3 days until the mice were sacrificed. The C57 mice were disinfected with 70% alcohol. The Lewis lung cancer tissue was removed, photographed and weighted Then, the subcutaneous tumors were fixed by formaldehyde for further analysis.

The effects of DDP and E003 on the tumor volume are shown in Table 3.

TABLE 3

| number | E003 | control | DDP |
|---|---|---|---|
| average ($mm^3$) | 284.2 | 748.1 | 473 |
| Inhibiting rate % | 0.62 | | 0.367 |

It can be seen from the results of Table 3 that the inhibiting effect of E003 in Lewis lung cancer cells is stronger than that of DDP.

EXAMPLE 7

The Synergetic Effects of the Inventive in Combination with other Antineoplastic Agent In this example, the effects of the compound E003 respectively in combination with Taxol, Adriamycin and Cisplatin as the other antineoplastic agent on growth of cancer cell were determined similarly to the method as described in Example 6. The compound E003 was administered together with, after or prior to the other antineoplastic agent, with an interval of 4.0 hours.

TABLE 4

The effect of E003 in combination with Taxol on growth of cancer cell

| Cell line | Time (hour) | Drugs and concentrations | Inhibition rate | effect |
|---|---|---|---|---|
| HL-60 | 24 | T0.01 − E5.0 | 0.47 ± 0.046 | A plus effect |
| | | T0.01 + E5.0 | 0.57 ± 0.022 | A plus effect |
| | | T0.001 − E5.0 | 0.46 ± 0.003 | A plus effect |
| | | T0.001 + E5.0 | 0.60 ± 0.016 | A plus effect |
| | | E5.0 − T0.01 | 0.55 ± 0.005 | A plus effect |
| | | E5.0 − T0.001 | 0.55 ± 0.020 | A plus effect |
| | | T0.01 | 0.27 ± 0.079 | |
| | | T0.001 | 0.02 ± 0.010 | |
| | | E5 | 0.33 ± 0.624 | |

TABLE 5

The effect of E003 in combination with Adriamycin on growth of cancer cell

| Cell line | Time (hour) | Drugs and concentrations | Inhibition rate | effect |
|---|---|---|---|---|
| HL-60 | 24 | A0.1 − E5.0 | 0.55 ± 0.002 | A plus effect |
| | | A0.1 + E5.0 | 0.55 ± 0.003 | A plus effect A |
| | | E5.0 − A0.1 | 0.52 ± 0.017 | plus effect |
| | | A0.1 | −0.07 ± 0.007 | |
| | | E5.0 | 0.33 ± 0.062 | |

TABLE 6

The effect of E003 in combination with Cisplatin on growth of cancer cell

| Cell line | Time (hour) | Drugs and concentrations | Inhibition rate | effect |
|---|---|---|---|---|
| HL-60 | 24 | DDP0.5 − E5.0 | 0.44 ± 0.014 | A plus effect |
| | | DDP0.5 + E5.0 | 0.55 ± 0.016 | A plus effect |
| | | E5.0 − DDP0.5 | 0.51 ± 0.004 | A plus effect |
| | | E5 − DDP5 | 0.51 ± 0.007 | A plus effect |

TABLE 6-continued

| Cell line | Time (hour) | Drugs and concentrations | Inhibition rate | effect |
|---|---|---|---|---|
| | | The effect of E003 in combination with Cisplatin on growth of cancer cell | | |
| | | DDP5 + E5 | 0.56 ± 0.007 | A plus effect |
| | | DDP0.5 − E5 | 0.44 ± 0.014 | A plus effect |
| | | DDP0.5 + E5 | 0.55 ± 0.016 | A plus effect |
| | | E5 − DDP0.5 | 0.51 ± 0.003 | A plus effect |
| | | DDP0.5 | 0.067 ± 0.014 | |
| | | DDP5 | 0.12 ± 0.032 | |
| | | E0.05 | −0.08 ± 0.031 | |
| | | E0.5 | 0.05 ± 0.0167 | |
| | | E5.0 | 033 ± 0.062 | |

Notes:
(1) Symbol and Concentration
E: Eb, in μmol/L; A: Adriamycin, in mg/L; DDP: Cisplatin, in μmol/L; and T: Taxol, in mg/L
(2) Administration mode
E and A are taken for example to explain the administration mode. E + A represents E and A are administrated at the same time with different concentrations as listed in Tabs. E − A represents administration of E is carried out 4 hours prior to that of A. A − E represents administration of A is carried out 4 hours prior to that of E. The others are similar to the above explanations.

EXAMPLE 8

Anti-Inflammation Activity

The anti-inflammatory effects of the test compounds E001, E002 and E003 were evaluated in xylene-induced ear oedema in mice. The mice were randomized into a no-treatment control group, three reference groups and three treatment groups. There are 10 animals in each group. The test compounds, saline and reference drugs (Indomethacin, Aspirin and Ebselen) were orally administered respectively. Ear oedema was induced by topical administration of xylene (0.5 ml per ear) to the inner surface of the right ear after 1 hour of the administration. After 2 hours, the mice were killed. The change in the ear's weight with diameter of 8 mm was measured with a precision micrometer. The inhibiting rate of each compound to the xylene-induced ear oedema was calculated in accordance with the ear weight, and the results were listed in Table 7.

TABLE 7

| sample | model | Ear oedema % | Inhibiting rate (%) | dosage |
|---|---|---|---|---|
| Saline | Ear oedema | 14.66 | | |
| Indo-meth-acin | Ear oedema | 19.89 | | 22 mg/kg |
| Aspirin | Ear oedema | 10.63 | | 200 mg/kg |
| Ebselen | Ear oedema | 6.22 | 68.72 (to indomethacin) 41.48 (to aspirin) | 50 mg/kg |
| E001 | Ear oedema | 4.81 | 75.81 (to indomethacin) 54.75 (to aspirin) | 50 mg/kg |
| E002 | Ear oedema | 9.85 | 50.47 (to indomethacin) 7.33 (to aspirin) | 50 mg/kg |
| E003 | Ear oedema | 7.91 | 60.20 (to indomethacin) 25.58 (to aspirin) | 50 mg/kg |

It can be concluded that the inventive compounds show higher anti-inflammatory activity than aspirin or indomethacin.

EXAMPLE 9

The Effects of the Inventive Compounds on Thrombosis

Male SD rats (300-400 g) were randomized into a no-treatment control group (0.25% CMC), an ASA reference group (0.25% CMC, a few Tween-80) and three treatment groups (the compounds B001, E002 and E003). There are 5 animals in each group. The inventive compounds and reference drugs were orally administered respectively in amount of 30 mg/kg. The animals were anesthetized with urethane after 1 hour of the administration. The neck artery was separated surgically and OT value was measured (the stimulating conditions: electricity, 3 mA; time, 180s). The results are listed in Table 8.

TABLE 8

| Drug | Average OT value (second) | SD | P value |
|---|---|---|---|
| CMC | 457.8 | | |
| E001* | 561.2 | 70.9 | 0.0270 |
| E002 | 481.4 | 73.4 | 0.5309 |
| E003** | 539.4 | 40.1 | 0.0057 |
| PX | 626 | 172.0 | 0.0936 |
| ASA | 588.2 | 83.8 | 0.0220 |

*P < 0.05,
**P < 0.05.

I claim:

1. A bisbenzisoselenazolonyl derivative of formula (I):

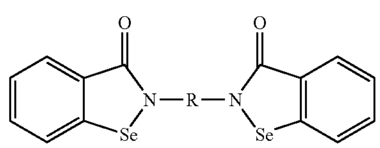

(I)

wherein:

R is biphenylidene, or triphenylidene or a pharmaceutically acceptable salt thereof.

2. The bisbenzisoselenazolonyl derivative according to claim 1, wherein R is a biphenylidene group.

3. A pharmaceutical composition comprising as an active ingredient the bisbenzisoselenazolonyl derivatives of general formula (I) according to claim 1 or their pharmaceutically acceptable salts and pharmaceutically acceptable excipient or carrier.

4. The pharmaceutical composition according to claim 3, further comprising other anti-inflammatory or antineoplastic agent or anti-thrombotics.

5. The pharmaceutical composition according to claim 4, wherein the other antineoplastic agent includes cisplatin, adriamycin, taxol or their combinations.

6. The pharmaceutical composition according to claim 4, wherein the other anti-inflammatory agent includes aspirin, indomethacin or their combinations.

7. The pharmaceutical composition according to claim 4, wherein the other anti-thrombotics includes aspirin.

* * * * *